United States Patent
Streett et al.

(10) Patent No.: US 10,041,923 B1
(45) Date of Patent: Aug. 7, 2018

(54) SPECTROPHOTOMETRIC SYSTEM FOR MEASURING WATER QUALITY

(71) Applicant: SWIFT ENGINEERING, INC., San Clemente, CA (US)

(72) Inventors: Andrew Streett, San Clemente, CA (US); Marc Rocklinger, Marina Del Rey, CA (US); Xuewu Liu, Largo, FL (US)

(73) Assignee: SWIFT ENGINEERING, INC., San Clemente, CA (US)

( * ) Notice: Subject to any disclaimer, the term of this patent is extended or adjusted under 35 U.S.C. 154(b) by 0 days.

(21) Appl. No.: 15/486,236

(22) Filed: Apr. 12, 2017

(51) Int. Cl.
| | |
|---|---|
| *G01N 33/18* | (2006.01) |
| *G01J 3/00* | (2006.01) |
| *G01N 21/80* | (2006.01) |
| *G01N 21/01* | (2006.01) |

(52) U.S. Cl.
CPC ............ *G01N 33/18* (2013.01); *G01N 21/01* (2013.01); *G01N 21/80* (2013.01); *G01N 2201/062* (2013.01); *G01N 2201/0826* (2013.01); *G01N 2201/0833* (2013.01)

(58) Field of Classification Search
None
See application file for complete search history.

(56) References Cited

U.S. PATENT DOCUMENTS

| | | | |
|---|---|---|---|
| 7,727,770 B2 | 6/2010 | Byrne et al. | |
| 7,943,391 B1 | 5/2011 | Byrne | |
| 8,071,031 B1 | 12/2011 | Byrne | |
| 8,077,311 B1 | 12/2011 | Byrne et al. | |
| 2005/0266516 A1* | 12/2005 | Kanipayor | C12Q 1/04 435/34 |
| 2007/0145249 A1* | 6/2007 | Kiesel | G01N 21/05 250/221 |

(Continued)

OTHER PUBLICATIONS

Sunburst Sensors, LLC, 2004, "SAMI-pH—Ocean pH Sensor," exact publication date unknown [retrieved on Jul. 20, 2017] www.sunburstsensors.com/products/oceanographic-ph-sensor.html, 2 pages.

(Continued)

*Primary Examiner* — Jill Alice Warden
(74) *Attorney, Agent, or Firm* — Perkins Coie LLP

(57) ABSTRACT

A system for measuring water quality parameters, such as pH, $CO_2$, alkalinity, and so forth, includes sensors or other measuring components integrated onto a circuit board. The circuit board may be contained within a submersible, water-tight housing. A spectrophotometer may be located on the circuit board to measure the wavelength and intensity of light transmitted through the water being tested. Sensors for measuring salinity, pressure, temperature, or other properties may also be included on or near the circuit board. A microcontroller for processing these measurements is located on the circuit board. System components used to direct and filter the water, such as certain pumps, filters, and so forth, may be included in the housing off of the circuit board. Integrating the sensors and other measuring components onto a circuit board allows for a compact, low-cost water-quality-measuring system that is capable of making very accurate and precise measurements.

20 Claims, 1 Drawing Sheet

(56) References Cited

U.S. PATENT DOCUMENTS

| | | | | |
|---|---|---|---|---|
| 2007/0188764 | A1* | 8/2007 | Nisper | G01J 3/02 356/446 |
| 2012/0140227 | A1* | 6/2012 | Willuweit | G01J 3/02 356/413 |
| 2014/0087476 | A1* | 3/2014 | Gu | G01N 31/22 436/125 |
| 2014/0273052 | A1* | 9/2014 | Reddy | G01N 33/1893 435/25 |

OTHER PUBLICATIONS

Xprize Foundation, 2015, "Montana Team Takes Home Both Top Prizes in $2 Million Wendy Schmidt Ocean Health Xprize," exact publication date unknown [retrieved on Jul. 20, 2017] www.oceanhealth.xprize.org/press-release/montana-team-takes-home-both-top-prizes-2-million-wendy-schmidt-ocean, 4 pages.

USPTO, "International Search Report and Written Opinion", for PCT/US18/26124, dated May 3, 2018.

* cited by examiner

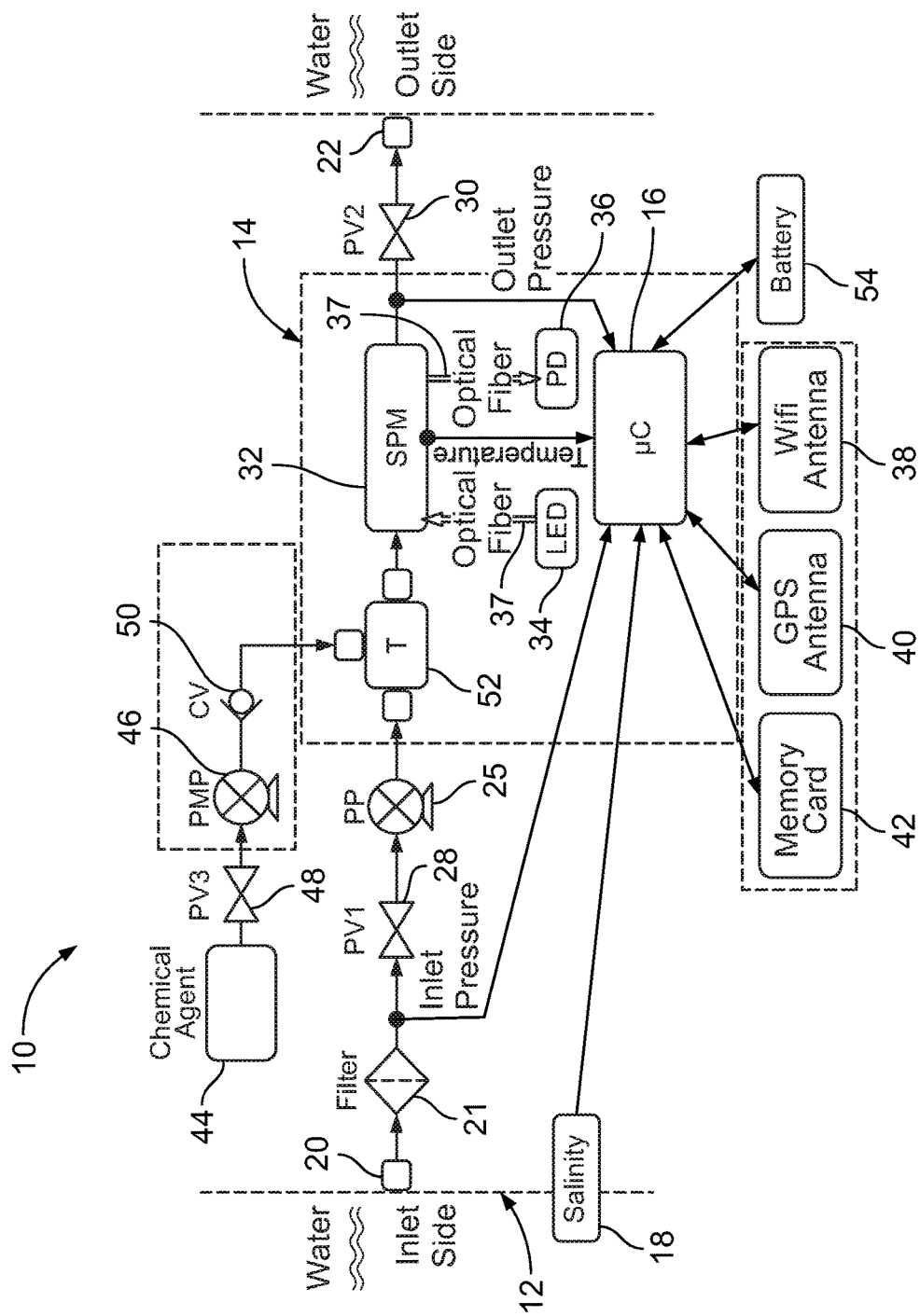

SPECTROPHOTOMETRIC SYSTEM FOR MEASURING WATER QUALITY

BACKGROUND

Chemical analyses of environmental parameters for water quality measurements are generally labor-intensive and require great care in sample collection and preservation. Automated in situ instruments offer numerous advantages. However, systems used to measure water quality parameters (e.g., pH and alkalinity) are typically large, expensive, and require repeated calibration. These systems generally include individual components that are operably connected to perform various water quality measurements. For these measurements to be reliable, they need to be performed with great degrees of accuracy and precision. Achieving highly accurate and precise measurements in existing systems, however, is challenging and cost prohibitive.

SUMMARY

A system for measuring water quality parameters, such as pH, $CO_2$, alkalinity, and so forth, includes sensors or other measuring components integrated onto a circuit board. The circuit board may be contained within a submersible, watertight housing for in situ measurements or developed as a benchtop flowing system. A spectrophotometer may be located on the circuit board to measure the wavelength and intensity of light transmitted through the water being tested. Sensors for measuring salinity, pressure, temperature, or other properties may also be included on or near the circuit board. A microcontroller for processing these measurements is located on the circuit board. System components used to direct and filter the water, such as certain pumps, switches, filters, and so forth, may be included in the housing off of the circuit board. Integrating the sensors and other measuring components onto a circuit board allows for a compact, low-cost water-quality-measuring system that is capable of making very accurate and precise measurements. Other features and advantages will appear hereinafter. The features described above can be used separately or together, or in various combinations of one or more of them.

BRIEF DESCRIPTION OF THE DRAWINGS

FIG. 1 is a schematic view of a water quality measuring system, according to one embodiment.

DETAILED DESCRIPTION OF THE DRAWINGS

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list. Further, unless otherwise specified, terms such as "attached" or "connected" are intended to include integral connections, as well as connections between physically separate components.

As shown in FIG. 1, in one embodiment, a spectrophotometric water-quality-measuring system 10 is contained within a submersible, watertight housing 12. The housing 12 may be made of fiberglass, Kevlar®, plastic, or another suitable material. The housing 12 is preferably "radio-frequency transparent" to allow transmission of signals, such as WiFi, Bluetooth®, or GPS signals, through the housing 12. In other embodiments, such as when the system is intended to be positioned above or near water, a watertight housing is not required. In these embodiments, a hose or similar device may be used to deliver water to the measuring system.

The system 10 may include components for measuring levels or concentrations of pH, $CO_2$, alkalinity, nitrates, nitrites, phosphates, ammonia, chlorine, nutrients, or other water quality parameters. To this end, the system may be configured to measure water quality parameters in sea water and fresh water applications, including oceans, lakes, rivers, fish tanks, pools, hydroponic gardens, and so forth. For ease of description, the below embodiments are generally directed to a system for measuring pH. Those skilled in the art will understand, however, that the system 10 could be used to measure other water quality parameters. For example, other metrics could be used to correlate optical measurements to certain chemical signatures, such as signatures of phosphates, nitrates, nitrites, and so forth. Those skilled in the art will also understand that the system could be modified to include additional or alternative sensors or measuring devices for measuring other water quality parameters.

The housing 12 includes an inlet 20 and an outlet 22 through which water to be tested ("test water") may enter and exit the housing 12. Once inside the housing 12, the test water travels within one or more tubes, pipes, or other suitable conduits that deliver the test water to the various sensors or measuring devices in the system 10, as described below. A filter 21 may be located downstream of the inlet 20 to remove seaweed and other debris from the test water before it enters the primary measuring region of the system. A pump, such as a peristaltic pump 25, may be located downstream of the filter 21 to pump the test water into the primary measuring region of the system 10.

In the illustrated embodiment, a circuit board 14, shown in dotted lines in FIG. 1, is contained in a watertight region of the housing 12. The circuit board 14 may be a four-inch by four-inch printed circuit board (PCB), for example, or may have any other suitable dimensions. In some embodiments, multiple circuit boards may be used. For ease of description, a single circuit board 14 will be discussed below.

The primary measuring and processing components of the system 10 may be located on the circuit board 14. A microcontroller 16, for example, that includes a processor for receiving and processing data to determine one or more water quality parameters, is located on the circuit board 14.

As is known to those of ordinary skill in the art, the pH of water may be calculated as a function of salinity, temperature, and changes in light intensity when a chemical agent is used. Thus, in the described embodiments, components for determining these properties are included in the system 10. A salinity sensor 18, for example, may be included at or near the housing inlet 20 to measure the concentration of dissolved salt in the test water as it enters the housing 12, or to measure the concentration of dissolved salt in the surrounding body of water, in general. The salinity sensor 18 transmits this data to the microcontroller 16 for processing. In some embodiments, additional or alternative sensors for measuring various water properties may be located external to the circuit board 14.

A chemical agent 44 for measuring pH may be introduced into the system 10 using a pump, such as a piezo micropump 46, located on or adjacent to the circuit board 14. A control valve 50 on or adjacent to the circuit board 14 may be used to regulate the flow of the chemical agent 44 into the primary measuring region of the system 10.

A T-connector 52 or similar device may be positioned downstream of the peristaltic pump 25 and the control valve 50. In one embodiment, the test water and the chemical agent 44 mix inside the T-connector 52 before further processing. The T-connector 52 may include multiple orifices, for example, that cause turbulent flow to facilitate this mixing of the test water and the chemical agent 44. Additionally or alternatively, powered mixing elements may be included inside the T-connector. Thus, the T-connector or other device may act as a mixing chamber.

A spectrophotometer 32 or optical cell for measuring light intensity may be included on the circuit board 14 downstream of the T-connector 52. The spectrophotometer 32 includes an optical chamber that receives the mixture of test water and the chemical agent 44. A light emitting diode (LED) 34, or other suitable light-generating device, may be used to transmit light at a predetermined wavelength through the mixture in the optical chamber. An optical receiver, such as a photodiode 36, may be positioned to receive the transmitted light and determine the light's wavelength and intensity after it passes through the mixture. The LED 34 and photodiode 36 may be connected to the optical chamber via fiber-optic light pipes 37 or other suitable light transmission devices. The spectrophotometer 32 may also include a temperature sensor that provides the temperature of the mixture in the optical chamber to the microcontroller 16.

Data from the various sensors, including data from the spectrophotometer 32, may be transmitted wirelessly or via a wired connection to the microcontroller 16. To attain high degrees of accuracy and precision, wired connections are preferred between the components residing on the circuit board 14.

A Wi-Fi antenna 38 or Bluetooth® antenna, or other suitable wireless adapter or device, may be included on the circuit board 14. Such a device may be used to transmit data from the system 10 to a receiving device, such as a mobile phone or tablet, or to a local area network (LAN). Additional components, such as a GPS antenna 40 for system position tracking, or a memory card 42 or other storage device for data logging, may optionally be included on the circuit board 14.

In some embodiments, pressure sensors, such as diaphragm sensors, may be included near the housing inlet 20 and outlet 22 to measure the inlet and outlet pressure of the system 10. These pressures may be used to verify that the system is functioning properly in a given external environment and that test water is moving properly through the system. They can also be used to ensure that the system 10 is not lowered to a depth at which the inlet pressure could damage or destroy pumps or other elements of the system 10.

Valves, such as pinch valves 28, 30, and 48, may be included in the housing 12 outside of the circuit board 14 to pinch the tubing through which the test water and chemical agent 48 travel. This pinching provides a physical barrier that prevents water or the chemical agent from entering the primary measuring region when the system 10 is underwater, travelling through waves, and so forth.

One or more batteries 54 may be included in the watertight housing 12, preferably off of the circuit board 14, to power the microcontroller 16 or other board components. In embodiments where the system is not intended to be submersed, the one or more batteries may be located inside or external to the housing.

By including the primary measurement components on a circuit board 14, electrical signal paths can be reduced, which reduces electrical dark current and resistance line losses. The system 10 can also be miniaturized, and the cost of the system can be reduced. The reduction of noise in the system 10 meaningfully increases its precision, while the use of one or more LEDs and fiber-optic light pipes increases the accuracy of the system 10, relative to existing systems. For example, line leads, optics positioning, and other features can be controlled within tight circuit-board tolerances. Further, the light burst from the LED 34 can be set for an exact duration, allowing for accurate wavelength measurements. As a result, it has been found that systems according to the present technology can make pH measurements that are accurate within 0.002 of the actual pH value, and precise within 0.001 of the actual pH value.

Further, by using spectrophotometric techniques, the optical components of the system 10 do not need to be calibrated frequently as they do in existing analog systems, such as pH probes. The system 10 may perform an internal calibration at startup, then be used without the need for additional calibration during a testing event. No external calibration is required.

In use, the system 10 is lowered into water, such as a body of seawater. In embodiments in which the system is positioned outside the water, test water may be delivered to the system via a hose or similar device. The test water enters the housing 12 through the inlet 20. The salinity sensor 18 detects the concentration of dissolved salt in the test water (or in the surrounding body of water) and transmits the data to the microcontroller 16. The test water then passes through the filter 21 to filter out any seaweed or other debris.

Next, the test water is pumped into the primary measuring region by the peristaltic pump 25. Meanwhile, the chemical agent 44 is pumped into the primary measuring region by the piezo micro-pump 46. The test water and the chemical agent 44 mix together inside the T connector 52.

The mixture then enters the spectrophotometer 32. The LED 34 transmits light through the mixture in the optical chamber of the spectrophotometer 32. The transmitted light is received by the photodiode 36, which determines the intensity of the transmitted light. The spectrophotometer 32 transmits this data, as well as temperature of the mixture in the optical chamber, to the microcontroller 16. The microcontroller 16 uses these data (salinity, temperature, LED output wavelength 1, and photodiode input wavelength) to calculate the pH of the test water, using known methods. The transmitted and processed data may be stored on the memory card 42. The test water then exits the housing 12 through the outlet 22.

Any of the above-described embodiments may be used alone or in combination with one another. Further, the water quality measuring system may include additional features not described herein. In some embodiments, certain components described as being located on the circuit board may alternatively be located off of the circuit board, and vice versa. While multiple embodiments have been described, various changes and substitutions may of course be made, without departing from the spirit and scope of the invention. The invention, therefore, should not be limited, except by the following claims and their equivalents.

What is claimed is:

1. A water quality measuring system, comprising:
   a housing;
   a circuit board in the housing;
   a spectrophotometer integrated onto the circuit board configured to determine at least one property of test water;
   a microcontroller on the circuit board in communication with the spectrophotometer that receives data about the at least one test-water property, the microcontroller configured to process the data to determine one or more water quality parameters.

2. The water quality measuring system of claim 1 wherein the spectrophotometer includes an optical chamber in communication with an LED and a photodiode via fiber-optic light pipes.

3. The water quality measuring system of claim 1 wherein the spectrophotometer is configured to transmit light intensity data to the microcontroller.

4. The water quality measuring system of claim 1 further comprising a pump located on or adjacent to the circuit board that delivers a chemical agent into the system upstream of the spectrophotometer.

5. The water quality measuring system of claim 4 further comprising a mixing chamber on the circuit board in which the chemical agent and the test water mix before entering the spectrophotometer.

6. The water quality measuring system of claim 1 further comprising an external sensor at or near an inlet to the housing.

7. The water quality measuring system of claim 6 wherein the external sensor comprises a salinity sensor.

8. The water quality measuring system of claim 1 wherein the housing is watertight and submersible, and the circuit board is contained within the watertight housing.

9. The water quality measuring system of claim 1 wherein the circuit board comprises a four-inch by four-inch printed circuit board.

10. The water quality measuring system of claim 1 further comprising at least one pump positioned between a housing inlet and the circuit board to pump the test water toward the spectrophotometer.

11. The water quality measuring system of claim 1 further comprising at least one pinch valve positioned between a housing inlet and the circuit board, the pinch valve preventing water from encountering the spectrophotometer when the pinch valve is in a closed position.

12. The water quality measuring system of claim 1 further comprising an antenna on the circuit board to wirelessly transmit data from the microcontroller to an external device.

13. The water quality measuring system of claim 1 wherein the spectrophotometer is configured to measure at least one water quality property used to determine levels or concentrations of pH, CO2, alkalinity, nitrates, nitrites, phosphates, ammonia, chlorine, or nutrients in the test water.

14. A water quality measuring system for determining at least one water quality parameter of test water, comprising:
    a housing;
    a salinity sensor in or on the housing;
    a circuit board in the housing;
    a spectrophotometer on the circuit board;
    a microcontroller on the circuit board in communication with the salinity sensor and the spectrophotometer, the microcontroller configured to process data from the salinity sensor and the spectrophotometer to determine pH of the test water.

15. The water quality measuring system of claim 14 wherein the microcontroller is configured to receive light intensity data and temperature data from the spectrophotometer, and salinity data from the salinity sensor.

16. The water quality measuring system of claim 14 wherein the housing is watertight and submersible.

17. The water quality measuring system of claim 14 further comprising a mixing chamber on the circuit board in which a chemical agent and the test water mix before entering the spectrophotometer.

18. A water quality measuring system, comprising:
    a housing;
    a circuit board in the housing;
    a spectrophotometer for determining one or more water quality parameters integrated onto the circuit board.

19. The water quality measuring system of claim 18 further comprising at least one device that contributes to determining the one or more water quality parameters located off of the circuit board.

20. The water quality measuring system of claim 18 further comprising a microcontroller on the circuit board in communication with the spectrophotometer, the microcontroller configured to process data from the spectrophotometer related to the one or more water quality parameters.

* * * * *